(12) United States Patent
Bertrand

(10) Patent No.: US 9,671,443 B2
(45) Date of Patent: Jun. 6, 2017

(54) DEVICE AND METHOD FOR MEASURING STATIC CHARGE ON FLYING INSECTS

(71) Applicant: Jacques C. Bertrand, Gainesville, FL (US)

(72) Inventor: Jacques C. Bertrand, Gainesville, FL (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 84 days.

(21) Appl. No.: 14/023,541

(22) Filed: Sep. 11, 2013

(65) Prior Publication Data

US 2015/0070030 A1 Mar. 12, 2015

(51) Int. Cl.
| | | |
|---|---|---|
| *G01N 27/02* | (2006.01) | |
| *G01R 27/26* | (2006.01) | |
| *G01R 29/24* | (2006.01) | |
| *A01M 1/02* | (2006.01) | |
| *A01M 1/06* | (2006.01) | |
| *A01M 1/14* | (2006.01) | |
| *G01N 27/60* | (2006.01) | |

(52) U.S. Cl.
CPC .......... *G01R 27/2611* (2013.01); *A01M 1/02* (2013.01); *A01M 1/06* (2013.01); *A01M 1/14* (2013.01); *G01R 29/24* (2013.01); *G01N 27/60* (2013.01)

(58) Field of Classification Search
CPC .......................... G01N 27/02; G01R 27/2611
USPC ................... 324/654, 457, 456; 43/113, 139
See application file for complete search history.

(56) References Cited

U.S. PATENT DOCUMENTS

| | | | | |
|---|---|---|---|---|
| 5,057,766 | A * | 10/1991 | Nakata et al. | 324/71.3 |
| 5,541,518 | A * | 7/1996 | Babbitt | G01P 13/0006 324/454 |
| 6,286,249 | B1* | 9/2001 | Miller et al. | 43/139 |
| 6,507,197 | B1* | 1/2003 | Itoh et al. | 324/456 |
| 7,654,034 | B2* | 2/2010 | Russik | 43/139 |
| 2005/0019361 | A1* | 1/2005 | Durand et al. | 424/405 |
| 2005/0248335 | A1* | 11/2005 | Care | 324/109 |
| 2006/0164094 | A1* | 7/2006 | Golder et al. | 324/452 |
| 2008/0181352 | A1* | 7/2008 | Hirafuji | A01M 1/026 377/16 |
| 2008/0298831 | A1* | 12/2008 | VanKouwenberg et al. | 399/92 |
| 2009/0045816 | A1* | 2/2009 | Robinson | 324/457 |
| 2009/0295400 | A1* | 12/2009 | Wilhelm | 324/452 |
| 2012/0066958 | A1* | 3/2012 | McGinnis, Jr. | 43/113 |

* cited by examiner

*Primary Examiner* — Son Le
*Assistant Examiner* — Akm Zakaria
(74) *Attorney, Agent, or Firm* — Albert M. Churilla; Ning Yang; Diane P. Tso

(57) ABSTRACT

A device and method of use for measuring the electrical charge of flying insects. The inventive device comprises measuring the charge induced by a flying insect and measuring the average of charge deposited on a metal screen due to the impact of multiple of insects on the screen.

11 Claims, 1 Drawing Sheet

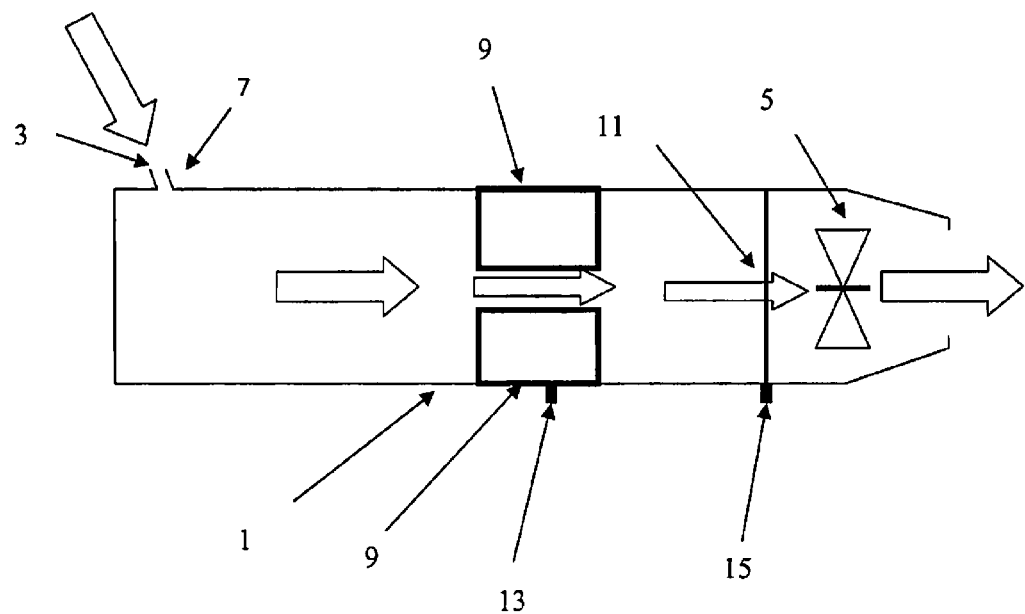

DEVICE AND METHOD FOR MEASURING STATIC CHARGE ON FLYING INSECTS

CROSS-REFERENCE TO RELATED APPLICATIONS

This application claims the benefit of provisional application, No. 61/700,448 filed Sep. 13, 2012.

BACKGROUND OF INVENTION

Field of Invention

The inventive subject matter relates to a device and method of measuring electrical charge on flying insects.

Background Art

Insecticides are typically applied to flying insects by spraying the insecticide with random coating or application based on chance collision with the spray.

Some pest traps comprise chemical lures, which attract the insect and are trapped by electrostatically charged particles (U.S. Pat. No. 6,041,543 to Howse) or are coated with electrostatically charged powder (U.S. Pat. No. 6,327,810 and U.S. Pat. No. 6,221,375 to P. E. Howse). However, no method of applying insecticides to flying insects by electrostatic charge currently exists. Furthermore, no efficient method to accurately measure static charge produced by flying insects is available. Devices and methods to obtain these measurements is of importance in designing methods to apply insecticides to flying insects using static charge with the minimum amount of pesticide, thus minimizing environmental impact.

SUMMARY OF THE INVENTION

The current invention relates to a device and method of measuring the electrical polarity and amount of electrical charge of flying insects. The electrical charge is principally due to the static charge developed as a result of their movement through the air and the movement of their wings.

The information derived from the method is applicable to the design of insecticidal materials and methods of application by electrical attraction.

BRIEF DESCRIPTION OF DRAWINGS

FIG. 1. Diagram of the device.

DETAILED DESCRIPTION OF PREFERRED EMBODIMENTS

Current methods of applying insecticides to flying insects typically involves spraying the material in the vicinity of the insects with the assumption that insects will be coated by randomly colliding with material momentarily suspended in the air as it slowly settles.

Insects create a charge as a result of the insect moving through the air and by the rapid motion of its wings. Application of materials by electrical charge attraction enables optimal efficacy of the materials. Furthermore, since the material effectiveness is optimized, the effect to the environment is minimized.

In order to design materials and optimal methods for application on flying insects, methods to determine the polarity and charge quantity are needed. An object of this invention is a device for measuring charge in flying insects.

Example 1: Insect Tube Device

The device, which is illustrated in FIG. 1, comprises a non-conductive hollow tube or tunnel (1), made of electrically non-conductive material, such as polycarbonate or other plastic or non-conductive glass or other coating to eliminate electrical charge. In one embodiment, the non-conductive hollow tube/tunnel (1) can be covered with grounded aluminum wire to prevent external electrical influence or charge.

At one end of the tube is an opening (3). The fan (5) provides a positive pressure into the device via the opening (3) and encourages insects down the tube (1), which are inserted, in a preferred embodiment, through a tube (7). The tube (7) can be angle to provide more efficient entry of a single insect.

As insects proceed down the non-conductive hollow tube (1) they will enter a metal center section (9), where any charge on the insect will induce an electrical field. The induced electrical field is then measured by the center measurement terminal (13). In this embodiment, introduction of insects through the metal center section (9) are controlled so that measurement of induced electrical fields via the center measurement terminal (13) is associated with a single flying insect.

As the insects proceed down the non-conductive hollow tube (1) toward the fan (5), they encounter the second measurement point, a screen (11), located adjacent to the fan (5), as illustrated in FIG. 1. The screen (11) is connected to a second terminal (15). In one embodiment, fly bait or other insect attractants can be used to promote insects flying onto the screen. Charge of the accumulated insects is measured. The charge via the second terminal (15) is averaged over the total number of insects impacting the screen and that are subsequently trapped onto the screen. To facilitate trapping of the insects, an adhesive can be applied to the screen (11). Efficient trapping of the insects prevents the insect from impacting the screen multiple times, which can impact accurate measurement of charge. The measurement at the screen (11) can measure average charge, predicated on the impact of multiple number insects.

An electrometer is connected via the center measurement terminal (13) and the terminal connected to the screen (15) to measure charge quantity. In a preferred embodiment, charge associated the static charge accumulated by a flying insect is capable of being measured to at least the femtocoulombs level. In this embodiment, the terminal connectors for the electrometer can be any number of different types of connectors for co-axial connection, preferably with quick-release features such as Bayonett Neill-Concelman (BNC) type connectors. In a preferred embodiment, connectors that are capable of are able to attenuate inherent electrical noise are used, such as Triax™ terminals. These connectors would be used on either or both the center measurement terminal (13) and screen terminal (15).

The fan (5) is preferably powered by a direct current (DC) power source. The fan speed, by adjustment of the power source to control for the flow of air through the tube (1). In a preferred embodiment, the fan is capable of running only in a single direction, to ensure that air is provided through tube opening (3).

Example 2: Method for Measuring Charge on a Flying Insect

Measurement of charge induced via by the flight of a flying insect is of importance in designing insecticides materials and methods of their use to optimally apply the insecticide materials to the insects in flight.

In a preferred embodiment, the inventive method measures the induction of an electrical field by a single insect.

Measurement can be conducted in a number of ways. As an illustration, measurement can be obtained as a single insect flies past metal plates or through a metal tube. In a preferred method, the device of Example 1 is utilized, wherein an insect flies through a metal tube and the induced electrical field is detected and measured by an electrometer.

In a preferred method, a second measurement of the total charge induced per insect is taken upon impact of a number of flying insects onto a metal screen. In this measurement, an average charge is measurement over the impacts of multiple insects. In a preferred embodiment, an adhesive is applied to the screen to ensure that the only a single impact per insect is measured. Any adhesive can be used as long as it solidly adheres the flying insect, preventing it from landing more than once.

In one embodiment and study, measurements of static charge were made following the insertion of flies (*Musca domestica*) into a device designed as in FIG. 1. The electrometer utilized was capable of measurement to femtocoulombs. In this example, the non-conductive hollow tube, or tube/tunnel (1) length was 54 inches, with an inside diameter of the tube/tunnel as 2.5 inches. The tube/tunnel was made of glass and covered with grounded aluminum wire to prevent external electoral influence. The measurement screen (11) was made of aluminum. The measurement screen was covered with a light coat of adhesive. In this embodiment, the adhesive was Catchmaster™ Glue (Atlantic Paste and Glue, 170 53$^{rd}$ Street, Brooklyn, N.Y.).

The conditions during the study consisted of a relative humidity of 30% and a temperature of 73° F. Flies were attracted toward the screen by fly bait and water. Flies were preconditioned by removing food and water for 4 hours prior to being released into the tube/tunnel. In the study, the results of which are shown in Table 1, 60 measurements were taken, using a total of 104 flies. The flies were removed in between each test and the screen was grounded to zero.

The study, using the example device, resulted in all the measurements giving a positive charge for each insect. The average for all flies was +19.0 pC, with a standard deviation of 5.5. The highest per fly charge for one measurement was +29.4 pC for test #15 (4 flies). The lowest per fly charge was +5 pC in test #18 (1 fly).

| Test # | # of flies landing on screen | charge on screen reading (pC)[1] | Ave. charge per fly (pC) | Test # | # flies on screen | Charge on screen (pC) | Ave. charge per fly (pC) |
|---|---|---|---|---|---|---|---|
| 1 | 1 | 17.0 | 17.0 | 31 | 2 | 22.0 | 11.0 |
| 2 | 1 | 8.0 | 8.0 | 32 | 2 | 48.6 | 24.3 |
| 3 | 1 | 18.0 | 18.0 | 33 | 1 | 18.0 | 18.0 |
| 4 | 1 | 11.8 | 11.8 | 34 | 1 | 7.0 | 7.0 |
| 5 | 2 | 28.0 | 14.0 | 35 | 3 | 48.0 | 16.0 |
| 6 | 1 | 17.5 | 17.5 | 36 | 2 | 34.0 | 17.0 |
| 7 | 2 | 48.0 | 24.0 | 37 | 3 | 43.5 | 14.5 |
| 8 | 1 | 17.0 | 17.0 | 38 | 2 | 34.0 | 17.0 |
| 9 | 2 | 36.0 | 18.0 | 39 | 3 | 87.0 | 29.0 |
| 10 | 1 | 21.0 | 21.0 | 40 | 2 | 23.0 | 11.5 |
| 11 | 2 | 44.0 | 22.0 | 41 | 2 | 40.0 | 20.0 |
| 12 | 1 | 19.0 | 19.0 | 42 | 1 | 21.5 | 21.5 |
| 13 | 1 | 20.0 | 20.0 | 43 | 1 | 27.3 | 27.3 |
| 14 | 2 | 54.0 | 27.0 | 44 | 2 | 50.0 | 25.0 |
| 15 | 4 | 117.6 | 29.4 | 45 | 1 | 32.0 | 32.0 |
| 16 | 2 | 30.0 | 15.0 | 46 | 2 | 40.0 | 20.0 |
| 17 | 1 | 19.0 | 19.0 | 47 | 1 | 18.0 | 18.0 |
| 18 | 1 | 5.0 | 5.0 | 48 | 1 | 22.3 | 22.3 |
| 19 | 3 | 62.1 | 20.7 | 49 | 2 | 46.0 | 23.0 |
| 20 | 2 | 49.0 | 24.5 | 50 | 2 | 32.0 | 16.0 |
| 21 | 1 | 21.0 | 21.0 | 51 | 3 | 81.0 | 27.0 |
| 22 | 2 | 51.0 | 25.5 | 52 | 2 | 37.0 | 18.5 |
| 23 | 1 | 17.0 | 17.0 | 53 | 1 | 19.5 | 19.5 |
| 24 | 2 | 38.0 | 19.0 | 54 | 1 | 14.5 | 14.5 |
| 25 | 1 | 22.0 | 22.0 | 55 | 2 | 40.4 | 20.2 |
| 26 | 2 | 42.0 | 21.0 | 56 | 2 | 35.4 | 17.7 |
| 27 | 2 | 46.0 | 23.0 | 57 | 1 | 18.5 | 18.5 |
| 28 | 4 | 60.0 | 15.0 | 58 | 1 | 18.4 | 18.4 |
| 29 | 2 | 18.0 | 9.0 | 59 | 2 | 37.0 | 18.5 |
| 30 | 1 | 22.5 | 22.5 | 60 | 3 | 37.5 | 12.5 |
| Ave. charge per fly (pC) = 19.0 (std dev. 5.5) | | | | | | | |

[1]picoCoulombs

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. A device for measuring electrical charge of a flying insect comprising an electrically non-conductive hollow tube containing a small opening and a large opening located at opposite ends of the non-conductive hollow tube; a metal hollow tube located inside the electrically non-conductive hollow tube and located with one end of the metal hollow tube beginning approximately 30% to 50% down the non-conductive hollow tube, wherein the metal hollow tube is electrically connected to a means for detecting electrical charge; a metal screen located between the metal hollow tube and the large opening, wherein the metal screen is electrically connected to a means for measuring the electrical charge of the screen, and a fan inside the hollow tube between the metal screen and the large opening, wherein said fan directs the flow of air from the small opening, through said screen, to the large opening, wherein insects are directed, by the air flow of said fan, to impact and become trapped on the screen, wherein said means for detecting electrical charge is via a co-axial connector that is capable of attenuating electrical noise of the device.

2. The device of claim 1, wherein said electrically non-conductive hollow tube is made of plastic or glass.

3. The device of claim 1, wherein said means for detecting electrical charge is an electrometer.

4. The device of claim 1, wherein said fan can run in two directions and is powered by a direct current power source.

5. The device of claim 1, wherein said means for measuring electrical charge can measure charge at down to at least the femtocoulomb level.

6. The device of claim 1, wherein said screen is coated with an adhesive.

7. The device of claim 1, wherein said non-conductive hollow tube is made of glass and covered with pounded aluminum wire to prevent external electrical influence.

8. The device of claim 1, wherein said small opening is angled relative to the non-conductive hollow tube.

9. A method of measuring electrical charge on an insect comprising: inserting one or more insects into a non-conductive hollow tube, wherein said non-conductive hollow tube is electrically connected to a means for detecting electrical charge, capturing one or more insects onto a screen by air flow imparted by a fan, wherein the screen is electrically connected to a means for measuring the electrical charge of the screen, counting the number of insects on the screen, and measuring the charge on the insects by the means for measuring the electrical charge connected to the non-conductive hollow tube and the screen.

10. The method of claim 9, wherein said method also includes averaging the charges of multiple flying insects after impacting onto a metal screen.

11. The method of claim 10, wherein said metal screen contains an adhesive layer to adhere insects impacting the screen.

\* \* \* \* \*